United States Patent [19]

Thompson et al.

[11] Patent Number: 5,251,486
[45] Date of Patent: Oct. 12, 1993

[54] METHOD OF ULTRASONIC MEASUREMENT OF TEXTURE

[75] Inventors: R. Bruce Thompson; John F. Smith, both of Ames, Iowa; Seung S. Lee, Taejon Ch'ungmam, Rep. of Korea; Yan Li, Ames, Iowa

[73] Assignee: Iowa State University Research Foundation, Inc., Ames, Iowa

[21] Appl. No.: 924,176

[22] Filed: Aug. 3, 1992

Related U.S. Application Data

[63] Continuation of Ser. No. 475,352, Feb. 5, 1990, abandoned, which is a continuation of Ser. No. 188,495, Apr. 29, 1988, Pat. No. 4,899,589.

[51] Int. Cl.$^5$ ............................................. G01N 24/00
[52] U.S. Cl. ........................................ 73/597; 73/602
[58] Field of Search .................. 73/597, 620, 632, 644, 73/602, 598

[56] References Cited

U.S. PATENT DOCUMENTS

| | | | |
|---|---|---|---|
| 2,536,128 | 1/1951 | Firestone et al. | 73/597 |
| 4,026,157 | 5/1977 | Goebbels | 73/432 |
| 4,165,649 | 8/1979 | Greer, Jr. | 73/644 |
| 4,353,256 | 10/1982 | Moorey | 73/597 |
| 4,372,163 | 2/1983 | Tittmann et al. | 73/602 |
| 4,432,234 | 2/1984 | Jones | 73/597 |
| 4,539,848 | 9/1985 | Takafuji et al. | 73/599 |
| 4,574,634 | 3/1986 | Pappano | 73/597 |
| 4,622,853 | 11/1986 | Leugers | 73/597 |
| 4,790,188 | 12/1988 | Bussiere et al. | 73/597 |
| 4,899,589 | 2/1990 | Thompson et al. | 73/597 |

FOREIGN PATENT DOCUMENTS

| | | |
|---|---|---|
| 58-2650 | 8/1983 | Japan. |
| 681366 | 8/1979 | U.S.S.R. |
| 894631 | 12/1981 | U.S.S.R. |

OTHER PUBLICATIONS

S. S. Lee, J. F. Smith & R. B. Thompson, "Inference of Crystallite Orientation Distribution Function From the Velocities of Unltrasonic Plate Modes", Nondestructive Characterization of Materials, J. F. Bussiere, ed. (Plenum Press, N.Y. in press).

Thompson, R. B., Lee, S. S., & Smith, J. F., "Angular Dependence of Ultrasonic Wave Propagation in a Stressed Orthorhombic Continuum Theory & Application to the Measurement of Stress and Texture", J. Acoust. Soc. Amer., 80, 921-931, Sep. 1986.

Thompson, R. B., Smith, J. F., & Lee, S. S., "Inference of Stress and Texture from the Angular Dependence Ultrasonic Plate Mode Velocities", Non-Destructive Evaluation of Microstructure For Process Control, H. N. G. Wadley, Editor (Asm. Metal Park, Ohio 1985), pp. 73-80.

R. Bruce Thompson, S. S. Lee, & J. F. Smith, "Relationship of the Wave Speed Anisotropies of Plane Wave and Guided Modes in Thin Orthorhombic Plates: Implication For Texture Characterization", Ames Laboratory, Iowa State University, Ames, Iowa 50011.

(List continued on next page.)

Primary Examiner—Louis Arana
Attorney, Agent, or Firm—Zarley, McKee, Thomte, Voorhees & Sease

[57] ABSTRACT

A method for measuring texture of metal plates or sheets using non-destructive ultrasonic investigation includes measuring the velocity of ultrasonic energy waves in lower order plate modes in one or more directions, and measuring phase velocity dispersion of higher order modes of the plate or sheet if needed. Texture or preferred grain orientation can be derived from these measurements with improves reliability and accuracy. The method can be utilized in production on moving metal plate or sheet.

62 Claims, 3 Drawing Sheets

OTHER PUBLICATIONS

Thompson, R. B. & Vasile, C. F., "An Elastic-wave Ellipsometer For Measurement of Material Property Variations", App. Phys. Lett. 34, 128–130 (1979).

S. S. Lee, J. F. Smith & R. B. Thompson, "Ultrasonic Techniques for the Quantitative Characterization of Texture": A Survey (verbally presented Oct. 1986.

G. J. Davies, D. J. Goodwill & J. S. Kallend, "Elastic and Plastic Anisotropy in Sheets of Cubic Metals", Metallurgical Transactions Jun. 1972, vol. 3, pp. 1627–1631 plus notes.

C. A. Stickels & P. R. Mould, "The Use of Young's Modulus for Predicting the Plastic-Strain Ratio of Low-Carbon Steel Sheets", Metallurgical Transactions, vol. 1, May 1970, pp. 1303–1312.

R. B. Thompson, S. S. Lee & J. F. Smith, "Relative Anisotropies of Plane Waves and Guided Modes in Thin Orthorphombic Plates: Implicatoin For Texture Characterization", 1987 Butterworth & Co., Ultrasonics 1987, vol. 25 May, pp. 133–137.

R. B. Thompson, J. F. Smith & S. S. Lee, "A Comparison of Ultrasonic and X-Ray Determinations of Texture in Thin Cu and Al Plates" no date.

(200) POLE
FIGURE COLD ROLLED
84%

ULTRASONIC (200) POLE
FIGURE ANNEALED 300°C

ULTRASONIC

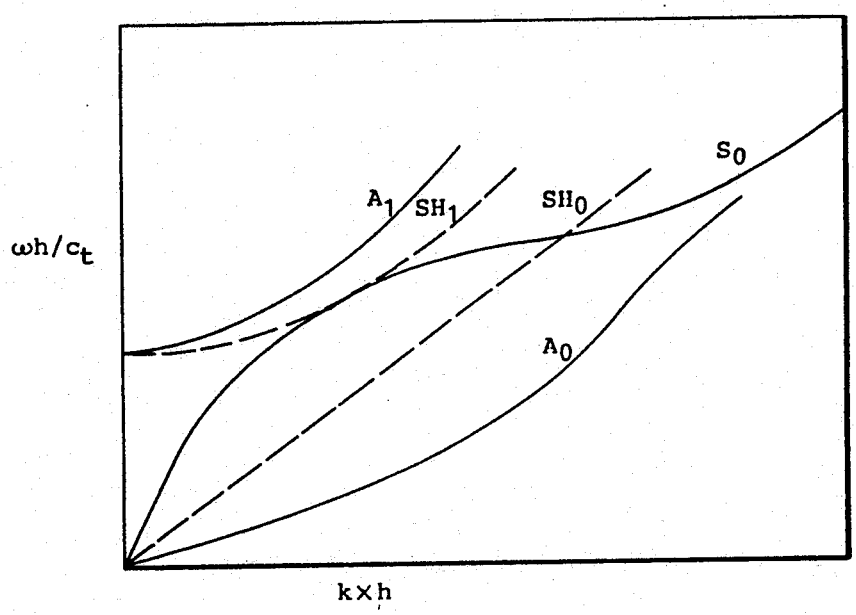
FIG_3

METHOD OF ULTRASONIC MEASUREMENT OF TEXTURE

GOVERNMENT PATENT RIGHTS

This invention was made with government support under government contract No. W-7405-ENG-82 awarded by the Department of Energy. The government has certain rights in the invention.

This is a of copending application Ser. No. 07/475,352 filed on Feb. 2, 1990, now abandoned which in turn is a continuation of U.S. patent Ser. No. 07/188,495 filed on Apr. 29, 1988 now U.S. Pat. No. 4,899,589.

BACKGROUND OF THE INVENTION a. Field of the Invention

The present invention relates to a method of measuring texture in metal plates or sheets, and particularly, pertains to a method of utilizing ultrasound to measure texture. The invention also pertains to a method for the prediction of mechanical formability of metal plates using ultrasound.

b. Problems in the Art

It would be greatly advantageous to be able to quickly and accurately discern texture in relatively thin plate and sheet material during its production. With such information, the manufacturing process could be efficiently controlled to produce a product of desired texture characteristics, or to correct texture deficiencies within a short time of when they occur. Knowledge of this texture is important, for example, in predicting the capability of the metal to be formed into parts of complex shape.

Previously, texture analysis required periodic sampling of the continuously produced sheet or plate material, and then utilization of x-ray or neutron diffraction techniques. Not only does this require destructive analysis from the periodically excised samples, such processes are time consuming and therefore cannot be used to immediately correct or change the production processes. Furthermore, x-ray processes give data only regarding the near surface of the material. Even though the material being analyzed is relatively thin sheet or plate, the texture characteristics can change drastically through its cross-section. The neutron processes provide information about the entire thickness of the material. However, the samples must be taken to a neutron source to perform the analysis. Therefore, the accuracy of these currently used processes is not as reliable or convenient as is desired.

Therefore, a real need exists for improvement regarding the monitoring and estimation of texture in sheet or plate materials such as rolled metal plate. It has previously been known that certain properties and inferences of texture can be derived from the analysis of received ultrasonic energy after it has been passed through the material. In particular, it has been discovered that texture might be inferred from measuring the differences in speed of ultrasonic energy in different directions through the material.

However, this knowledge has applied to thick metal pieces in which the wave properties are uninfluenced by the part surfaces They must be modified to be applied to metal plates and sheets, which is the geometry often encountered when one wishes to control texture.

The present inventors have worked with theoretical foundation for such non-destructive texture estimation. However up until the present invention, the theoretical bases for valid and accurate texture estimation had not been discovered. In fact, previous published works on the matter had been incorrect in the assumptions and theory for certain parts of the analysis.

It is therefore a principal object of the present invention to improve over or solve the deficiencies and problems in the art.

Another object of the present invention is to provide a method of ultrasonic measurement of texture which provides efficient and accurate estimates of texture in plate or sheet material.

A further object of the present invention is to provide a method as above described which is non-destructive to the material being analyzed.

Another object of the present invention is to provide a method as above described which can be easily adapted to be used in the area of and during production of the material.

Another object of the present invention is to provide a method as above described which does not require complex, time-consuming, or impractical processes or equipment to derive accurate texture estimations.

A further object of the present invention is to provide a method as above described which utilizes ultrasound as an interrogating medium.

These and other objects, features, and advantages of the invention will become more apparent with reference to the accompanying specification and claims.

SUMMARY OF THE INVENTION

A method of ultrasonic measurement of texture utilizes advances in mathematical and theoretical understanding of measurement of the anisotropy of ultrasound wave velocities through a plate material, along with advances in technology and instrumentation, to allow accurate, reliable and efficient non-destructive estimation of texture in such material. The process can be easily adapted to be used directly in the manufacturing environment to give feedback in a matter of minutes to control manufacturing and to monitor output.

The method measures the velocity of ultrasonic energy carried by low order plate modes of the material in one or more directions. Utilizing mathematical theory for describing texture in metal plate, the velocity measurements can be used to solve for the texture. In some cases, however, the answers may be erroneously influenced by certain idealizations in the theory. To complete the texture characterization under those conditions, the velocity of higher order plate modes regarding the ultrasonic waves is also measured. Information from such measurements provides an alternate scheme to provide the information needed for mathematical estimation of texture.

The low order modes in which velocity is measured are $S_o$ and $SH_o$, in the preferred embodiment of the invention. The higher order modes include the $SH_n$ modes. The invention therefore allows accurate estimation of texture without having to utilize the commonly used destructive x-ray or neutron diffraction techniques. Additionally, the method can be in continuous operation and give quick "in-process" feedback. The manufacturing process can therefore be adjusted to change or correct texture characteristics according to desire. The value of such an in-process method is enormous to the rolled metal-plate industry. The application of the invention can also be applied to similar materials.

BRIEF DESCRIPTION OF THE DRAWINGS

FIG. 3 a graphic depiction of the higher order mode used in one to obtain improved information on the coefficient $W_{400}$.

DETAILED DESCRIPTION OF THE PREFERRED EMBODIMENT

With reference to the drawings, a preferred embodiment of the present invention will now be described. It is to be understood that this description is not by way of limitation to the invention, but is for purposes of understanding the invention and disclosing one preferred way in which it can be carried out.

Figure 1:
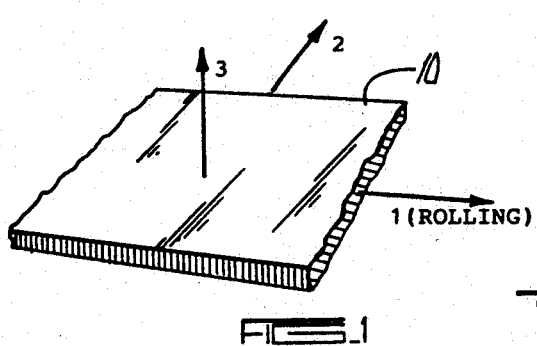
FIG. 1 is a perspective view of a rolled plate material, also showing a coordinate system designating the rolling direction, transverse direction, and thickness direction.

To aid in an understanding of the invention, FIG. 1 schematically depicts a rolled metal plate 10. Arrows 1, 2, and 3 depict the rolling, transverse, and thickness directions, respectively, of plate 10. Any reference to the "plane" of plate 10 refers to the plane defined by directions 1 and 2. It can thus be seen that in the preferred embodiment, the invention can be utilized on rolled metal plate 10 to determine characteristics such as texture and preferred orientation of grain. With such knowledge, characteristics such as hardness, grain size, ductility, strength and formability can be estimated. It is important to understand that the present invention allows the determination of these texture characteristics "in-process"; that is, contrary to conventional methods of destructive x-ray or neutron diffraction, the present invention allows non-destructive evaluation as the plate is being produced, and directly on the plate production line. The advantages of this much quicker, local, non-destructive method are many.

The present invention thus requires the generation and introduction of appropriate ultrasonic energy into plate 10. It then also requires the ability to receive the transmitted ultrasonic energy and to precisely deduce the velocity of propagation. In some cases, the velocity will be frequency dependent, and this dispersion must be taken into account. The preferred embodiment of the invention thus requires appropriate means and methods to send, receive, and process the ultrasound for these purposes. One embodiment for doing so is disclosed by S. J. Wormley and R. B. Thompson, entitled "A SEMI-AUTOMATIC SYSTEM FOR ULTRASONIC MEASUREMENT OF TEXTURE, in *Review of Process in Quantitative Non-destructive Evaluation*, 6A, D. O. Thompson and D. E. Chimenti Eds. (Plenum Press, N.Y. 1987), p. 951 by Wormley and Thompson, and hereby incorporated by reference.

The central concept of the present invention is to utilize non-destructive ultrasonic interrogation to derive the preferred grain orientation (also called texture) of a metal plate or sheet from measurements of anisotropy of ultrasonic wave speeds through the material. The fundamental basis for measuring ultrasound velocity is disclosed in R. B. Thompson, J. F. Smith, and S. S. Lee, "Inference of Stress and Texture from the Angular Dependence Ultrasonic Plate Mode Velocities", *Non-Destructive Evaluation of Microstructure for Process Control*, H. N. G. Wadley, Editor (Asm. Metal Park, Ohio 1985), pp. 73-80; and R. B. Thompson, S. S. Lee, and J. F. Smith, "Angular Dependence of Ultrasonic Wave Propagation in a Stressed Orthorhombic Continuum: Theory and Application to the Measurement of Stress and Texture", *J. Acoust. Soc. Amer.*, 80, 921-931, Sep. 1986), both of which are incorporated by reference herein.

The preferred orientation of grains (texture) in a metal plate is described by the series $$w(\xi, \psi, \phi) = \sum_{l=0}^{\infty} \sum_{m=-l}^{l} \sum_{n=-l}^{l} W_{lmn} Z_{lmn}(\xi) e^{-im\psi} e^{-in\phi} \quad \text{Eq. (1)}$$

where $\xi = \cos \theta$, W is a distribution function describing the probability that a grain will have a particular orientation, $\xi$, $\psi$, $\Omega$, are Euler angles defining crystallite orientation, and $Z_{lmn}$ are generalized Legendre functions. $W_{lmn}$ are constant coefficients which can be derived in plates such as rolled metal plate 10 by measuring ultrasonic velocities when the variable letter term "l" of $W_{lmn}$ is less than or equal to the number 4.

While this general relationship was disclosed in the above cited articles, certain incorrect assumptions and mathematical analysis were utilized which did not and cannot accurately derive the desired texture characteristics.

The present invention therefore accurately and reliably derives texture in a rolled metal plate utilizing equation (1) and the following steps.

The Voigt procedure to compute the average elastic constants of a polycrystal of a cubic material described by a crystallite orientation distribution function (CODF) leads to the following result:

$$c_{11} = L + \frac{12\sqrt{2} \, c^0}{5} x^2 \left[ W_{400} - \frac{2\sqrt{10}}{3} W_{420} + \frac{\sqrt{70}}{3} W_{440} \right] \quad (2a)$$

$$c_{22} = L + \frac{12\sqrt{2} \, c^0}{35} x^2 \left[ W_{400} - \frac{2\sqrt{10}}{3} W_{420} + \frac{\sqrt{70}}{3} W_{440} \right] \quad (2b)$$

$$c_{33} = L + \frac{32\sqrt{2} \, c^0}{35} x^2 W_{400} \quad (2c)$$

$$c_{12} = P + \frac{4\sqrt{2} \, c^0}{35} x^2 [W_{400} - \sqrt{70} \, W_{440}] \quad (2d)$$

$$c_{13} = P - \frac{16\sqrt{2} \, c^0}{35} x^2 \left[ W_{400} - \sqrt{\frac{5}{2}} W_{420} \right] \quad (2e)$$

$$c_{23} = P - \frac{16\sqrt{2} \, c^0}{35} x^2 \left[ W_{400} + \sqrt{\frac{5}{2}} W_{420} \right] \quad (2f)$$

$$c_{44} = T - \frac{16\sqrt{2} \, c^0}{35} x^2 \left[ W_{400} + \sqrt{\frac{5}{2}} W_{420} \right] \quad (2g)$$

-continued $$C_{55} = T - \frac{16\sqrt{2}\,C^0}{35} x^2 \left[ W_{400} + \sqrt{\frac{5}{2}}\, W_{420} \right] \quad (2h)$$

$$C_{66} = T + \frac{4\sqrt{2}\,C^0}{35} x^2 [W_{400} + \sqrt{70}\, W_{440}] \quad (2i)$$

where in the Voigt approximation, the isotropic elastic moduli are defined as $L = C_{11}^0 - C^0/5$, $P = C_{12}^0 + C^0/5$, $T = C_{44}^0 + C^0/5$, the elastic anisotropy is defined as $C^0 = C_{11}^0 - C_{12}^0 - 2C_{44}^0$ and $C_{11}^0$, $C_{12}^0$, and $C_{44}^0$ are the single crystal elastic constants of cubic crystallites. For these equations, it is assumed that plate 10 is homogeneous and has macroscopic orthotropic (orthorhombic) symmetry defined by the three mutually perpendicular mirror planes which can be associated with directions 1, 2, and 3 in FIG. 1.

Equations 2 show that the elastic constants of cubic polycrystals are defined by only three coefficients of the CODF expansion namely, $W_{400}$, $W_{420}$, and $W_{440}$. When the single crystal constants are known, the Voigt averaging procedure can be used (in cases where plate 10 has weak anistropy). Only these three orientation distribution coefficients (ODC's) need to be measured to fully specify the texture to the fullest degree possible, utilizing linear ultrasonic measurements.

Texture can induce variations in these ODC's to change the anisotropy in wave speed. Wave speed anisotropies can also be induced by the presence of stress, as is discussed in the printed publication entitled "Inference of Stress & Texture from the Angular Dependence Ultrasonic Plate Mode Velocities" identified previously. While the present application can be applied to plate 10 having stress effects, for purposes of the preferred embodiment, it will be assumed that all stress effects have been eliminated from the data via the previous art and the characterization of texture will be a prime consideration.

Recently, advances have been made in the theoretical understanding of the relationship between the speeds of the waves in plates and the ODC's ($W_{lmn}$). Also, recent developments in measuring equipment (such as development of electromagnetic acoustic transducers (EMAT's)) allow ultrasonic velocity measurements to be made rapidly with no couplant. EMAT's are ideally suited to real time measurements in actual production environments; that is, directly in the process line for rolled metal plate 10. The invention can therefore be used for direct non-destructive contemporaneous in-process control.

It has been found that the preferred EMAT probe geometries include the use of meander coil and periodic permanent magnet geometries.

In the preferred embodiment of the invention, unknown ODC's $W_{400}$, $W_{420}$ and $W_{440}$ are deduced. Coefficients W420 and $W_{440}$ are deducted from variations of wave velocities in the plane of plate 10, as determined by the elastic constant anisotropy. In principle, $W_{420}$ could be determined from the difference of $C_{11}$ and $C_{22}$ as deduced from a comparison of the velocities of longitudinal waves propagating in the rolling and transverse directions, directions 1 and 2 in FIG. 1, respectively. However, such simplistic ideas do not give quantitatively correct results as discussed below. The significance of the new art will be first put in perspective by a comparison to prior knowledge.

Prior art has shown that $W_{400}$ can be measured in different thicknesses of plate 10 as follows For thick plates, for which it is possible to resolve in time the echoes of shear waves propagating through the thickness, $W_{420}$ can be determined from the relative arrival times of signals polarized along directions 1 and 2 (rolling and transverse) in FIG. 1. This amounts to a comparison of $C_{44}$ and $C_{55}$. Precise knowledge of the plate thickness is not essential since it is the same for both polarizations. The properties of the material are averaged through the thickness for the particular volume of plate through which the ultrasonic beam passes. Parameters $W_{420}$ and $W_{440}$ both can be deduced from the angular dependence of the Rayleigh wave (elastic surface wave) velocity on the plane of plate 10. Separation of the two is made possible by the different angular variations (COS $2\theta$ and COS $4\theta$) of the variations governed by the two coefficients. The plate 10 is sampled to a thickness equal to the penetration of the Rayleigh wave (approximately one wavelength). The results are independent of thickness as long as the lower surface of plate 10 does not interact with the Rayleigh wave. $W_{440}$ can also be deduced from the angular variation of the velocity of surface skinning horizontally polarized shear waves. The material properties are sensed in a near-surface region, although the penetration depth is somewhat greater than for Rayleigh waves, and depends upon the details of the experimental geometry.

For thinner plates, somewhat different considerations are involved. The velocities of longitudinal waves propagating along the rolling and transverse direction may be affected by the boundaries of the plate surfaces. It may be difficult to resolve echoes of signals propagating through the thickness of plate 10. Also, Rayleigh waves and surface skimming horizontally polarized shear waves may be influenced by the proximity of plates 10's lower surface, as these solutions assumes a medium bound by only one surface.

As revealed herein, these difficulties are overcome by analyzing the received data in terms of the guided elastic modes of plate 10. In one preferred embodiment, coefficients $W_{400}$, $W_{420}$ and $W_{440}$ are deducted from the speeds of the $SH_o$ and $S_o$ modes propagating in the plane of the plate. By referring to FIG. 3, it can be seen that the phase velocity ($\omega/k$) of the $S_o$ mode is essentially constant at low frequencies, as indicated by the essentially constant slope of that portion of the dispersion curve. It is in this region that the measurements are preferred to be made.

Figure 2:
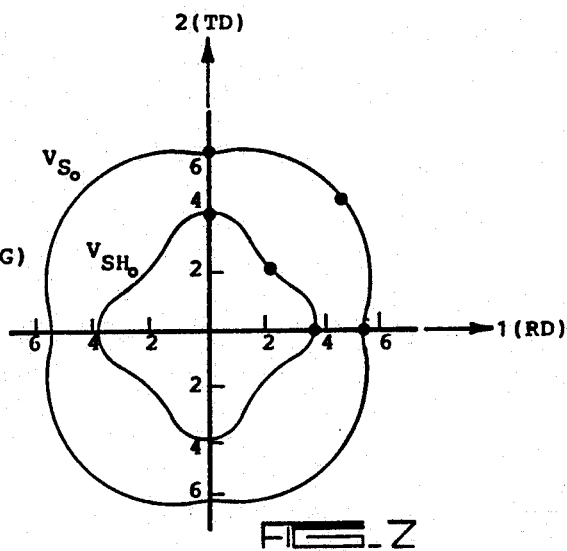
FIG. 2 is a graphic depiction of the measurements utilized in determination of the $W_{400}$, $W_{420}$ and $W_{440}$ coefficients from the low order plate modes.
Figure 4:
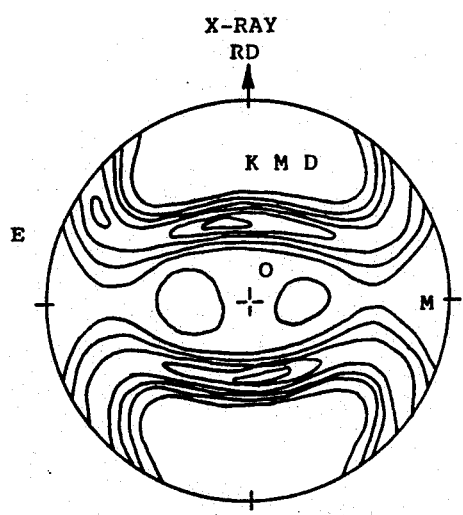
FIGS. 4-7 are comparisons between x-ray diffraction techniques and ultrasonic techniques and ultrasonic techniques according to the invention for measurement of texture in copper.
Figure 5:
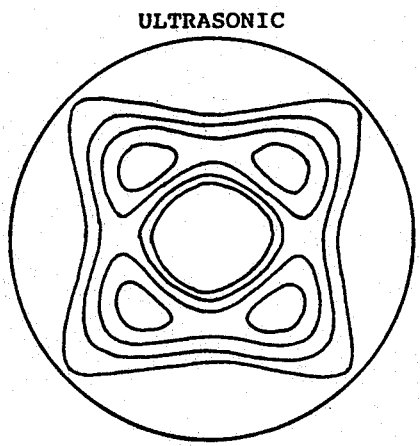
Figure 6:
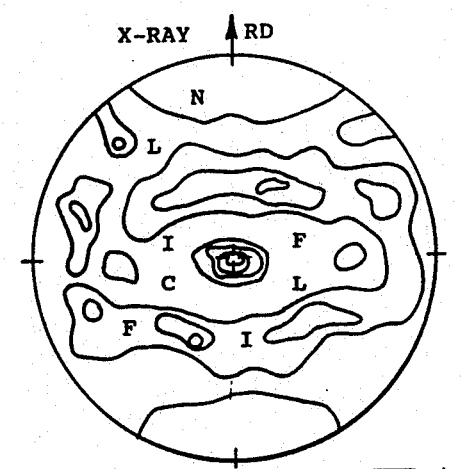
Figure 7:
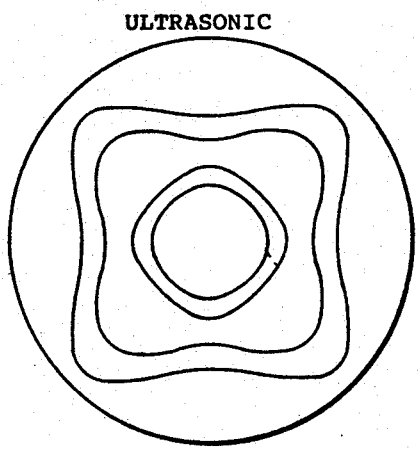

By referring to FIG. 2, it can be seen that the angular dependence of ultrasonic wave speeds of these $SH_o$ (horizontally polarized shear) and $S_o$ (extensional) modes of plate 10 can be used. Both the $SH_o$ and $S_o$ wave speeds are measured at 0°, 45° and 90° with respect to rolling direction 1 (in FIG. 1). The angular dependences of these speeds has the same functional form as that of plane waves, but the parameters are modified by the differences between the plane wave and plate solutions. The recognition of this difference is an important aspect of this invention. Reference is taken to R. B. Thompson, S. S. Lee and J. R. Smith, 37 Relative Anisotropies of Plane Waves and Guided Modes in Thin Orthorhombic Plates: Implication for Texture Characterization", *Ultrasonics*, 1987, vol. 25, May, pp. 133-137, which is incorporated by reference herein. The formulae relating velocity to the $W_{400}$, $W_{420}$ and $W_{440}$ coefficients are:

$$W_{440} = \frac{\sqrt{35}\,\rho}{16\pi^2 C}\,[V^2_{SH0}(45°) - V^2_{SH0}(0°)] \quad \text{Eq. 3(a)}$$

$$W_{440} = \frac{\sqrt{35}\,\rho}{32\pi^2 C}\,[V^2_{S0}(0°) + V^2_{S0}(90°) - 2V^2_{S0}(45°)] \quad \text{Eq. 3(b)}$$

$$W_{420} = \frac{7\sqrt{5}\,\rho}{32\pi^2(1 + 2P/L)C}\,[V^2_{S0}(90°) - V^2_{S0}(0°)] \quad \text{Eq. 3(c)}$$

$$W_{400} = \frac{35\sqrt{2}\,\rho}{16\pi^2 C}\,[V^2_{SH0}(45°) + V^2_{SH0}(0°) - 2(T/\rho)] \quad \text{Eq. 3(d)}$$

$$W_{400} = \frac{35\sqrt{2}\,\rho}{32\pi^2[3 + 8(P/L) + 8(P/L)^2]C}\,[V^2_{S0}(0°) + V^2_{S0}(90°) + 2V^2_{S0}(45°) - 4(L - P^2/L)/\rho] \quad \text{Eq. 3(e)}$$

Examination of Equations (3a–3e) shows that $W_{420}$ and $W_{440}$ are predicted from differences in measured velocities while $W_{400}$ depends on the sums of measured velocity. Thus $W_{420}$ and $W_{440}$ can be determined from angular determinations of velocities while $W_{400}$ depends on the absolute velocity. Because of this difference, practical difficulties sometimes are encountered on the determination of $W_{400}$. The inference of $W_{400}$ from absolute measurements depends on the absolute accuracy of the computation of polycrystalline average elastic constants. Since the accuracy of those computations is considerably better for relative variations than for absolute values, this additional potential for significant error also exists. Moreover, when attempting to deduce $W_{400}$ from $S_o$ mode measurements, the data must also be corrected from the slight frequency dependence of the $S_o$ mode velocity at low frequencies. These may not be limiting factors for alloys of simple metallurgical structure, but may cause greater problems for more complex alloys.

Therefore, the present invention includes alternate procedures for determining $W_{400}$ from the phase velocity dispersion of the higher order plate modes. In one approach, one deduces the elastic constants $C_{44}$, $C_{55}$ and $C_{66}$ from the data and calculates $W_{400}$ in terms of the differences in these elastic constants. This eliminates the possible errors in both velocity measurement and computation of polycrystalline average elastic constants as would occur in attempting to determine $W_{400}$ from absolute velocity measurements. In another approach, one examines the degree of splitting of the dispersion curves for two modes which would normally be tangent in the untextured case (see FIG. 3). These two approaches are described in greater detail below.

The speeds of the higher order horizontally polarized shear modes, denoted $SH_n$ in FIG. 3, depend only on $C_{44}$, $C_{55}$ and $C_{66}$ when the waves are propagating along the rolling and transverse directions denoted by the 1 and 2 axes in FIG. 1. If these constants can be determined by fitting measured velocity data to the theory, examination of Eq. (2) shows that enough information is available to determine the three unknown coefficients.

In one embodiment, one observes the frequency of waves which can be excited by a transducer having a fixed periodicity, which defines the wavelength of the waves at that frequency. One has thus specified one point $(\omega, k)$ on the dispersion curve. $C_{44}$, $C_{55}$, and $C_{66}$ can be determined by analyzing the results of several such measurements in terms of the dispersion curves of the plate modes. The thickness of plate 10 is not particularly critical for $C_{44}$ and $C_{55}$ as they depend on thickness and similar waves. However, thickness must be precisely known for determining $C_{66}$, as these methods average the elastic properties through the thickness of plate 10 over the path transversed by the ultrasonic waves.

A strong motivation for use of this approach is in the determination of $W_{400}$, when it cannot be obtained from absolute measurements of the velocity of the $S_o$ mode as discussed in the previous embodiment. Utilizing equations 2(g)–2(i) and the elastic constants $C_{44}$, $C_{55}$ and $C_{66}$ deduced by measuring the phase velocity dispersion of the higher order plate modes of plate 10, it follows that:

$$W_{400} = \frac{\sqrt{70}}{5}\,W_{440} - \frac{7(C_{44} + C_{55} - 2C_{66})}{8\sqrt{2}\,C\,\pi^2}$$

Utilizing this step, the problems of utilizing absolute measurements are overcome since determination of $W_{400}$ now depends on relative values of $C_{44} + C_{55} - 2C_{66}$. However, it is essential to precisely know the thickness of the plate because of the aforementioned dependence of $C_{66}$ on this parameter.

In the other preferred embodiment depending on the dispersion curves of the higher order plate modes, concentration is focused on the point at which the $SH_l$ and $S_o$ mode dispersion curves are tangent, as illustrated in FIG. 3. This is the behavior that is characteristic in an isotropic plate ($W_{400} = W_{420} = W_{440} = W_{440} = 0$). However, when anistropy is present, this tangency no longer occurs. The $SH_l$ and $S_o$ mode dispersion curves either overlap, with two points of intersection, or do not cross at all. Modeling of ultrasonic wave propagation in anistropy plates having elastic constants described by Eq. (2) shows that $W_{400}$ can be quantitatively inferred from measurements of the degree of overlap or lack thereof. This technique has the additional advantage of not requiring a precise knowledge of the plate thickness, since the dispersion curves of both modes are shifted in a similar fashion by thickness changes.

An instrument suitable for the experimental measurement of the properties of these modes in this region has been disclosed by R. B. Thompson and C. F. Vasile, "An Elastic-wave Ellipsometer for Measurement of Material Property Variations", Appl. Phys. Lett. 34, 128–130 (1979).

Operation of the invention can be advantageous in many applications It can be used in process control of sheet metal production and quality control of incoming materials for aerospace, automotive, packaging, and many other processes and industries.

Experimental results have shown that the present invention compares favorably with x-ray diffraction.

Table I below shows the experimental results for $W_{440}$ utilizing the present method for aluminum and copper sheet or plate, as compared to x-ray diffraction results.

TABLE I

| Comparison of $W_{440}$ Predicted by X-ray and Ultrasonic Techniques | | | |
|---|---|---|---|
| | X-ray | $SH_o$ Ultrasonics | $S_o$ Ultrasonics |
| Aluminum | −0.00362 | −0.00594 | −0.00583 |

TABLE I-continued

Comparison of $W_{440}$ Predicted by X-ray and Ultrasonic Techniques

| | X-ray | $SH_o$ Ultrasonics | $S_o$ Ultrasonics |
|---|---|---|---|
| Copper | −0.00319 | −0.00302 | −0.00288 |

In Table I, the samples used were 1100 aluminum and commercially pure copper. With regard to copper, the values of $W_{440}$ deduced from the two ultrasonic modes are in good agreement with the x-ray diffraction data. With respect to the aluminum, the two ultrasonic values are in agreement but differ from the x-ray value by a considerable margin, nearer 50%.

Both x-ray and ultrasonic techniques predicted considerably smaller values for $W_{420}$ for those samples.

FIGS. 4-7 presents a comparison of x-ray and ultrasonic pole figures for plate reduced to 84%, and the same plate after annealing for 0.5 hours at 300° C. Although the ultrasonic pole figures do not contain the same degree of detail, the general structure of the texture and its change with annealing are clearly revealed. The ultrasonic figures (FIGS. 5 and 7) show only the first few terms in the series equation 1 which results in the lesser detail.

Figure 8:
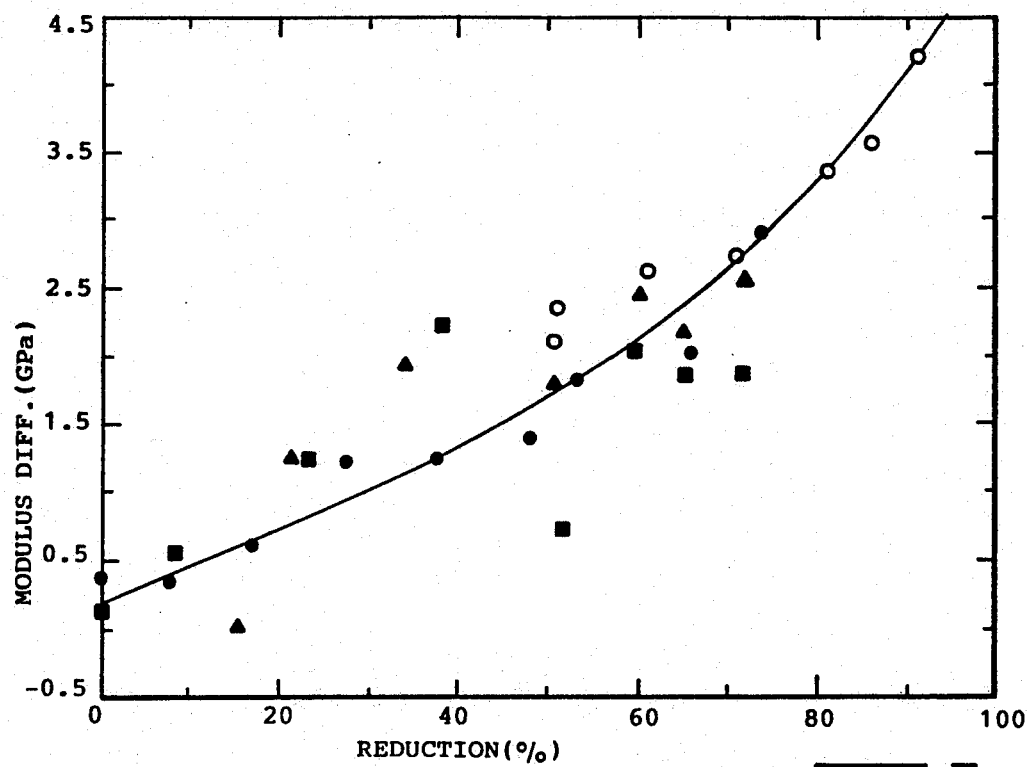
FIGS. 8 and 9 are graphic depictions of comparison of results between the ultrasonic method of the present invention and x-ray diffraction.
Figure 9:
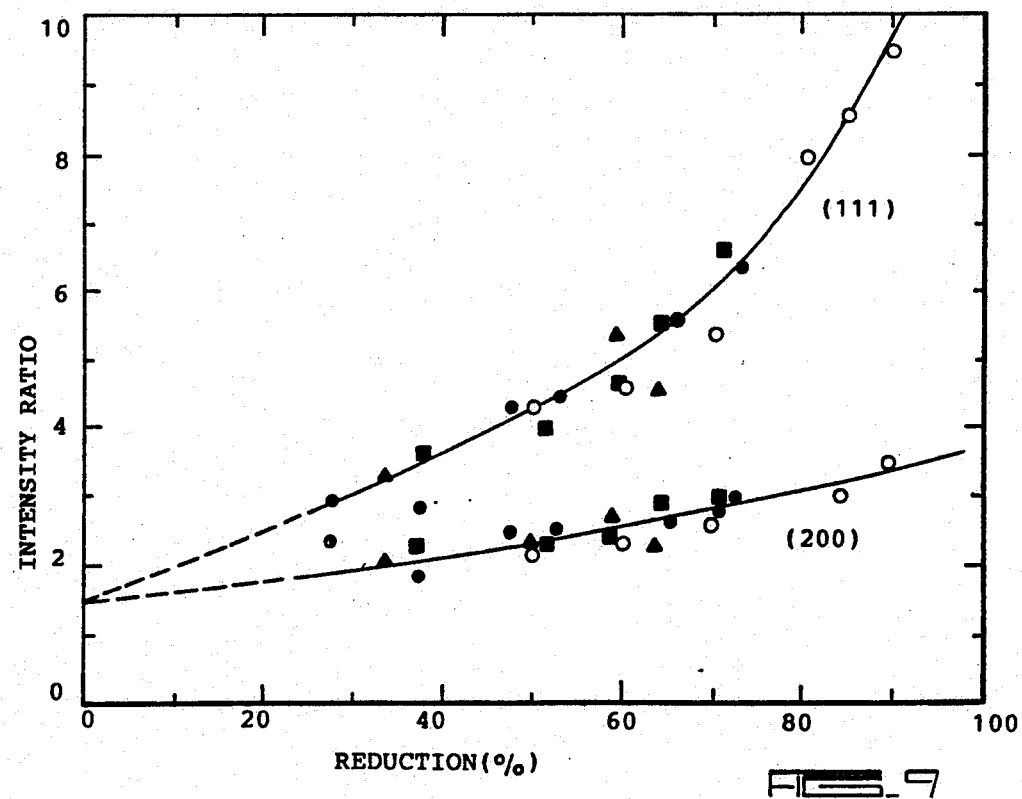

For further comparison, FIGS. 8 and 9 qualitatively compare the modulus difference ($C_{44} - C_{55}$, which is proportional to $W_{420}$) as a function of thickness reduction to the normalized intensity of what are referred to as the (111) and (200) poles as determined by x-rays. The evolution of the texture is indicated in a similar manner by each parameter.

FIGS. 4-9 therefore show the general good agreement between the present invention and x-ray diffraction. The advantages of the present invention over x-ray diffraction techniques provides a real and valuable advance in the art.

The included preferred embodiment is given by way of example only, and not by way of limitation to the invention, which is solely described by the claims herein. Variations obvious to one skilled in the art will be included within the invention defined by the claims.

What is claimed is:

1. A method for analyzing texture of sheet material comprised of polycrystals of various crystallite symmetries and which has a rolling direction and boundary surfaces, using non-destructive ultrasonic investigation of the sheet material, comprising the steps of:
   measuring the velocity of ultrasonic propagating in at least one plate mode of the sheet material in one or more directions relative to the rolling direction of the sheet material; and
   deriving texture-related characteristics from said measurements by analyzing the absolute values and anisotropies of said plate mode velocity measurements in terms of theory of wave propagation in anisotropic plates, which simultaneously takes into account the influence of boundary surfaces of the sheet material and anisotropies in elastic stiffnesses on the velocity of plate mode propagation and which thereby recognizes that the anisotropies of plate mode velocities are different than those of plane waves because of the influence of the boundary surfaces.

2. The method of claim 1 wherein each plate mode is a lower order plate mode of the sheet material.

3. The method of claim 2 wherein the lower order plate mode is $S_o$.

4. The method of claim 2 wherein the lower order plate mode is $SH_o$.

5. The method of claim 2 wherein the lower order plate mode is selected from the set consisting of $S_o$ and $SH_o$.

6. The method of claim 1 wherein the preferred orientation of grains or texture of the material is defined by the equation $$w(\xi, \psi, \phi) = \sum_{l=0}^{\infty} \sum_{m=-l}^{l} \sum_{n=-l}^{l} W_{lmn} Z_{lmn}(\xi) e^{-im\psi} e^{-in\phi}$$

where $\theta$, $\psi$, and $\phi$ are Euler angles defining crystallite orientation, $\xi = \cos\theta$, $Z_{lmn}$ are generalized Legendre functions, $W_{lmn}$ are constants known as orientation distribution coefficients where, m, and n are summation indices defining basis functions $Z_{lmn}(\xi)$, $e^{-im\psi}$ and $e^{-in\phi}$, $w(\xi, \psi, \phi)$ measures the probability that the crystallite will have the specified orientation, and where the plate mode velocity measurements are utilized to determine the parameters $W_{lmn}$ defining texture of the material.

7. The method of claim 6 wherein the variable l in the term $W_{lmn}$ is less than or equal to 4.

8. The method of claim 6 wherein the variable m of the term $W_{lmn}$ is less than or equal to 4.

9. The method of claim 6 wherein the variable n of the term $W_{lmn}$ is 0.

10. The method of claim 6 wherein the velocities in at least one plate mode are used to derive $W_{400}$, $W_{420}$ and $W_{440}$.

11. The method of claim 10 wherein $W_{400}$ is derived utilizing the equation $$W_{400} = \frac{\sqrt{70}}{5} W_{440} - \frac{7(C_{44} + C_{55} - 2C_{66})}{8\sqrt{2} \, C^o \pi^2}$$

where $C_{44}$, $C_{55}$, and $C_{66}$ are elastic constants and $C^o$ is a measure of the elastic anisotropy of a single crystal, given by $C^o = C_{11}^o - C_{12}^o - 2C_{44}^o$ where $C_{11}^o$, $C_{12}^o$ and $C_{44}^o$ are single crystal elastic constants.

12. The method of claim 10 wherein $W_{400}$ is derived from plots of dispersion curves for higher order plate modes of the sheet material.

13. The method of claim 1 wherein the material comprises cubic metals.

14. The method of claim 13 wherein the cubic metals include but are not limited to the set comprising copper, aluminum, and iron.

15. The method of claim 1 wherein said measurements of velocity include one or more absolute velocity measurements.

16. The method of claim 1 where said measurements of velocity include one or more relative velocity measurements.

17. The method of claim 1 wherein said measurements of velocity include at least one relative velocity measurement and at least one absolute velocity measurement.

18. The method of claim 1 wherein the sheet material comprises material of hexagonal crystal symmetry.

19. The method of claim 18 wherein the sheet material of hexagonal crystal symmetry is taken from the set including but not limited to titanium and zirconium.

20. The method of claim 1 wherein the sheet material includes plate material.

21. The method of claim 1 wherein the material comprises metal sheet.

22. The method of claim 1 wherein results of the measurements are used to predict properties of the material.

23. The method of claim 22 wherein properties predicted include formability parameters of the material.

24. The method for measuring texture related properties of sheet material of polycrystals of various crystallite symmetries, which has a rolling direction in the plane of the sheet material and has boundary surfaces, using non-destructive ultrasonic investigation of the material, comprising the steps of:

imposing ultrasonic energy, propagating in at least one plate mode of the sheet material, through the sheet material;

measuring the velocity of said ultrasonic energy in one or more directions relative to the rolling direction of the sheet material; and deriving texture-related characteristics from said measurements of velocity by analyzing the absolute values and anisotropies of said plate mode velocity measurements in terms of theory of wave propagation in anisotropic plates, which simultaneously takes into account influences of the boundary surfaces of the sheet material and anisotropies in elastic stiffness on the velocity of plate mode propagation.

25. The method of claim 24 wherein each plate mode is a lower order plate mode.

26. The method of claim 25 wherein the lower order plate mode is $S_o$.

27. The method of claim 25 wherein the lower order plate mode is $SH_o$.

28. The method of claim 25 wherein the lower order plate mode is selected from the set consisting of $S_o$ and $SH_o$.

29. The method of claim 24 wherein the preferred orientation of grains or texture of the sheet material is defined by the equation $$w(\xi, \psi, \Phi) = \sum_{l=0}^{\infty} \sum_{m=-l}^{l} \sum_{n=-l}^{l} W_{lmn} Z_{lmn}(\xi) e^{-im\psi} e^{-in\Phi}$$

where $\theta$, $\psi$, and $\phi$ are Euler angles defining crystallite orientation, $\xi = \cos\theta$, $Z_{lmn}$ are generalized Legendre functions, $W_{lmn}$ are constants known as orientation distribution coefficients where l, m, and n are summation indices defining the basis functions $Z_{lmn}(\xi)$, $e^{-im\psi}$ and $e^{-in\phi}$, $w(\xi, \psi, \phi)$ measures the probability that the crystallite will have the specified orientation, and where the velocity measurements are utilized to determine the parameters $W_{lmn}$ defining texture of the sheet material.

30. The method of claim 29 wherein the variable l in the term $W_{lmn}$ is less than or equal to 4.

31. The method of claim 29 wherein the variable m in of the term $W_{lmn}$ is less than or equal to 4.

32. The method of claim 29 wherein the variable n of the term $W_{lmn}$ is 0.

33. The method of claim 30 wherein coefficients $W_{400}$, $W_{420}$ and $W_{440}$ are all derived by velocity measurement.

34. The method claim 24 wherein derivation of the measurements is frequency dependent.

35. The method claim 24 wherein said measurements of velocity include one or more absolute velocity measurements.

36. The method of claim 24 where said measurements of velocity include one or more relative velocity measurements.

37. The method of claim 33 wherein coefficients $W_{420}$ and $W_{440}$ are derived by velocity measurements and a comparison of angular dependencies of those measurements in at least one low order plate mode of the sheet material, and coefficient $W_{400}$ is derived from measurements of dispersion of higher order plate modes of the sheet material if the thickness of the material is precisely known.

38. The method of claim 24 wherein the texture-related properties include at least formability parameters.

39. The method of claim 33 wherein the coefficients $W_{420}$ and $W_{440}$ are derived by velocity measurements and comparison of angular dependencies of the measurements, and the coefficient $W_{400}$ is derived by plotting dispersion curves of higher order modes of the material, without precise knowledge of the thickness of the sheet material.

40. The method of claim 39 wherein the coefficient $W_{400}$ is determined on the basis of whether dispersion curves of modes of the sheet material are tangent, cross, or approach one another.

41. The method of claim 40 wherein frequency of the ultrasound is varied to derive the dispersion curves.

42. A method for measuring texture of a bounded media of polycrystals of cubic crystallite symmetry having a rolling direction and boundary surfaces using non-destructive ultrasonic investigation of the bounded media, comprising the steps of:

imposing ultrasonic energy, propagating in at least one plate mode of the bounded media, through the bounded media;

measuring the velocity of the ultrasonic energy in one or more directions relative to the rolling direction of the bounded media;

selecting at least one of the following steps, while considering the influences of the boundary surfaces of the bounded media on the plate mode velocity measurements by analyzing the absolute values and anisotropies of said plate mode velocity measurements in terms of theory of wave propagation in anisotropic plates;

comparing angular dependencies of the plate mode velocity measurements and deriving coefficients $W_{420}$ and $W_{440}$ from the plate mode velocity measurements; and using absolute values of averages of the plate mode velocity measurements to obtain coefficient $W_{400}$.

43. A method for estimating texture-related properties of a bounded media having a rolling direction and boundary surfaces and through which can be propagated ultrasonic energy in the form of ultrasonic plate modes, comprising the steps of:

propagating the ultrasonic energy in a plurality of angular directions relative to the rolling direction of the bounded media, and measuring, in at least one ultrasonic plate mode, the velocity of the ultrasonic energy for each angular direction and ultrasonic plate mode combination; and estimating texture-related characteristics of the bounded media from the absolute values and angular dependence of the velocities of each ultrasonic plate mode considering the effects of the boundary surfaces of the bounded media on the plate mode velocity measurements by analyzing the absolute values and anisotropies of said plate mode velocity measurement in terms of theory of wave propagation in anisotropic plates.

44. The method of claim 43 wherein the plurality of angular directions include 0°, 45° and 90° relative to the rolling direction of the bounded media.

45. The method of claim 43 wherein the plate mode is a low order ultrasonic plate mode.

46. The method of claim 45 wherein the plate mode is the $S_o$ mode.

47. The method of claim 45 wherein the plate mode is $SH_o$ mode.

48. The method of claim 45 wherein the plate mode is taken from the set comprising $S_o$ and $SH_o$.

49. The method of claim 45 wherein two plate modes are utilized taken from the set of low order plate modes comprising $S_o$ and $SH_o$.

50. The method of claim 43 wherein the texture-related properties include at least formability parameters.

51. The method of claim 43 wherein the bounded media includes polycrystals of various crystallite symmetries.

52. The method of claim 51 wherein the bounded media comprises polycrystals of cubic and hexagonal symmetries.

53. The method of claim 52 wherein the bounded media comprises metal plate.

54. The method of claim 52 wherein the bounded media comprises metal sheet.

55. The method of claim 42 wherein the bounded media is metal plate material.

56. The method claim 42 wherein the bounded media is metal sheet material.

57. The method of claim 10 wherein $W_{lmn}$ and related formability parameters are derived directly from the plate mode velocity measurements.

58. The method of claim 57 wherein $W_{400}$ is derived from a quantity $$V^2_{SHo}(45°) + V^2_{SHo}(0°),$$

where $V_{SHo}$ defines the plate mode velocity for the $SH_o$ mode, and 45° and 0° define the angular direction of the ultrasound with respect to the rolling direction of the plate.

59. The method of claim 57 wherein $W_{400}$ is derived from a quantity $$V^2_{So}(0°) + V^2_{So}(90°) + 2V^2_{So}(45°),$$

where $V_{So}$ indicates the $S_o$ plate mode velocity measurement, and 0°, 45°, and 90° represent the direction of the ultrasound relative to the rolling direction of the plate.

60. The method of claim 57 wherein $W_{440}$ is derived from a quantity $$V^2_{SHo}(45°) - V^2_{SHo}(0°),$$

where $V_{SHo}$ indicates the $SH_o$ plate mode velocity measurement, and 0°, 45°, represent the direction of the ultrasound relative to the rolling direction of the plate.

61. The method of claim 57 wherein $W_{440}$ is derived from a quantity $$V^2_{So}(0+) + V^2_{So}(90°) - V^2_{So}(45°),$$

where $V_{So}$ indicates the $S_o$ plate mode velocity measurement, and 0°, 45° and 90°, represent the direction of the ultrasound relative to the rolling direction of the plate.

62. The method of claim 57 wherein $W_{420}$ is derived from a quantity $$V^2_{So}(90°) - V^2_{So}(0°),$$

where $V_{So}$ indicates the $S_o$ plate mode velocity measurement, and 90°, 0°, represent the direction of the ultrasound relative to the rolling direction of the plate.

* * * * *